United States Patent
Tanaka et al.

(10) Patent No.: US 8,216,152 B2
(45) Date of Patent: Jul. 10, 2012

(54) FINGER ARTERIAL ELASTICITY MEASURING PROGRAM, FINGER ARTERIAL ELASTICITY MEASURING DEVICE AND FINGER ARTERIAL ELASTICITY MESAURING METHOD

(75) Inventors: Gohichi Tanaka, Sapporo (JP); Yukihiro Sawada, Sapporo (JP)

(73) Assignee: Sapporo Medical University, Hokkaido (JP)

(*) Notice: Subject to any disclaimer, the term of this patent is extended or adjusted under 35 U.S.C. 154(b) by 516 days.

(21) Appl. No.: 12/449,816

(22) PCT Filed: Feb. 12, 2008

(86) PCT No.: PCT/JP2008/052232
§ 371 (c)(1),
(2), (4) Date: Aug. 27, 2009

(87) PCT Pub. No.: WO2008/105229
PCT Pub. Date: Sep. 4, 2008

(65) Prior Publication Data
US 2010/0004546 A1    Jan. 7, 2010

(30) Foreign Application Priority Data
Feb. 28, 2007  (JP) ................................. 2007-048652

(51) Int. Cl.
*A61B 5/02* (2006.01)
(52) U.S. Cl. ........ 600/504; 600/480; 600/481; 600/490; 600/494
(58) Field of Classification Search ........... 600/480–507
See application file for complete search history.

(56) References Cited

U.S. PATENT DOCUMENTS
2004/0059236 A1 *  3/2004  Margulies et al. ............ 600/500
(Continued)

FOREIGN PATENT DOCUMENTS
JP  2004-236730   8/2004

OTHER PUBLICATIONS
Goichi Tanaka, "Simplified Assessment Method of Cardiovascular Health..", The Japanese Journal of Physiological Psychology.., Aug. 31, 2006, pp. 94-95, vol. 24, No. 12.
(Continued)

*Primary Examiner* — Patricia Mallari
*Assistant Examiner* — Eric Messersmith
(74) *Attorney, Agent, or Firm* — DLA Piper LLP (US)

(57) ABSTRACT

PROBLEMS TO BE SOLVED: A finger arterial elasticity measuring program, a finger arterial elasticity measuring device and a finger arterial elasticity measuring method are provided for making it possible to measure an elasticity index of a finger artery in accordance with a pulse wave of a finger artery without measuring a blood pressure in evaluating the elasticity of the finger artery related to the degree of arterial sclerosis in an easy and least expensive manner.

MEANS FOR SOLVING THE PROBLEMS: A computer functioning by a finger arterial elasticity measuring program includes a pulse wave data memory unit 42, a cuff pressure data memory unit 43, a normalized pulse volume (NPV) calculating unit 52 for dividing an amplitude ($\Delta I$) of an alternate component of a pulse wave by an average value of direct components (I) to calculate NPV, a relative cuff pressure ($P_r$) calculating unit 53 for calculating a difference between a cuff pressure at the maximum amplitude of the pulse wave and each cuff pressure as $P_r$, an FEI calculating unit 54 for calculating a linear regression slope (n) of the following expression (1) as an elasticity index of a finger artery: $\ln(NPV)=\ln(bn)-n\cdot P_r$ . . . (1) where b is a constant.

3 Claims, 4 Drawing Sheets

U.S. PATENT DOCUMENTS

2004/0092832 A1* 5/2004 Schnall et al. ............... 600/490
2006/0009700 A1* 1/2006 Brumfield et al. ............ 600/504

OTHER PUBLICATIONS

Hisami Horiguchi, et al., "Finger arterial elasticity, a novel assessment of . . . ", The Japanese Journal of Physiological Psychology.., Jun. 25, 2006, pp. 17-47, vol. 19, No. 1.

Joji Andoh, et al., "Application of photoelectric pulse wave measurement", BME, 1990, pp. 24-32, Japan.

Van Assendelft Ow, "Light Absorption Spectra of Haemoglobin Derivatives", Royal Vangorcum in Assen, Dec. 31, 1970, pp. 47-73.

Michael T. Allen et al., "Hemoconcentration and stress . . . ", The Biological Psychology, 1995, pp. 1-27, Elsevier Science Ireland Ltd.

Matthew F. Muldoon et al., "Acute Cholesterol Responses to Mental Stress and Change in Posture", The Original Investigation, Apr. 1992, pp. 775-780, vol. 152.

Toshio Ozawa, "Pulse Pressure Determination in Clinical Practice", Sep. 22, 2005, pp. 9-15, Clinical Blood Pressure Pulse Wave Workshop.

* cited by examiner

[Fig.1]
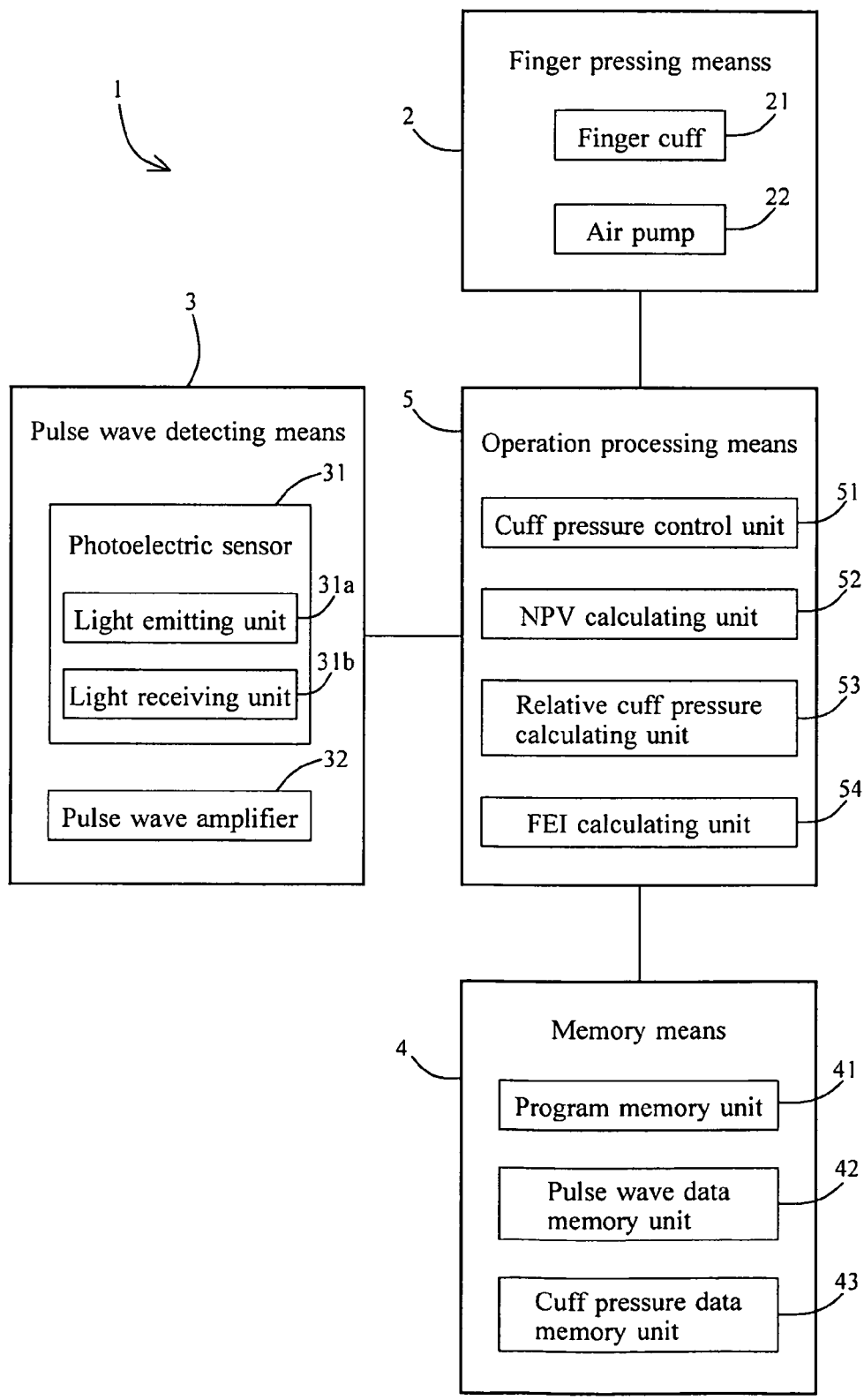

[Fig.2]
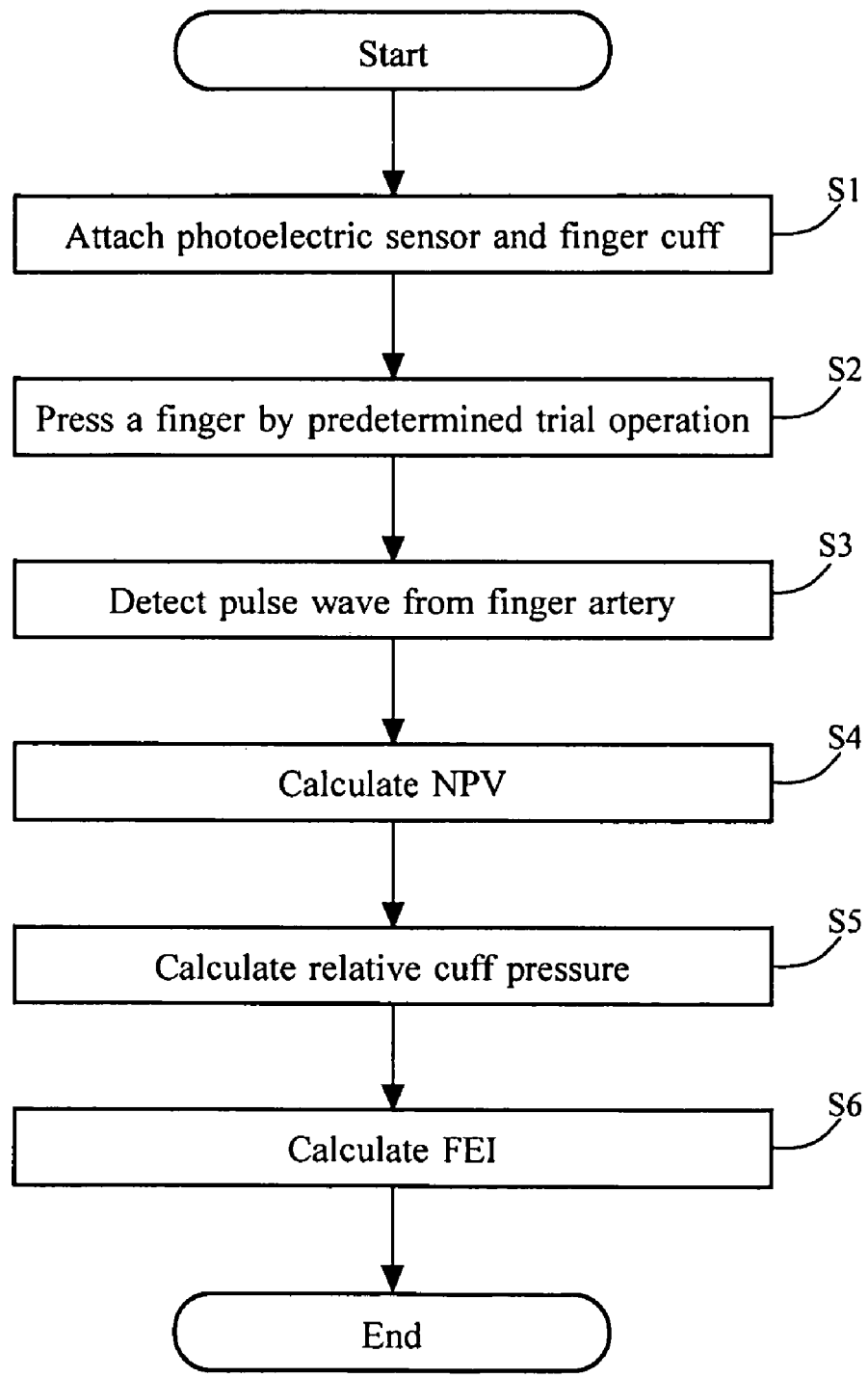

[Fig.3]
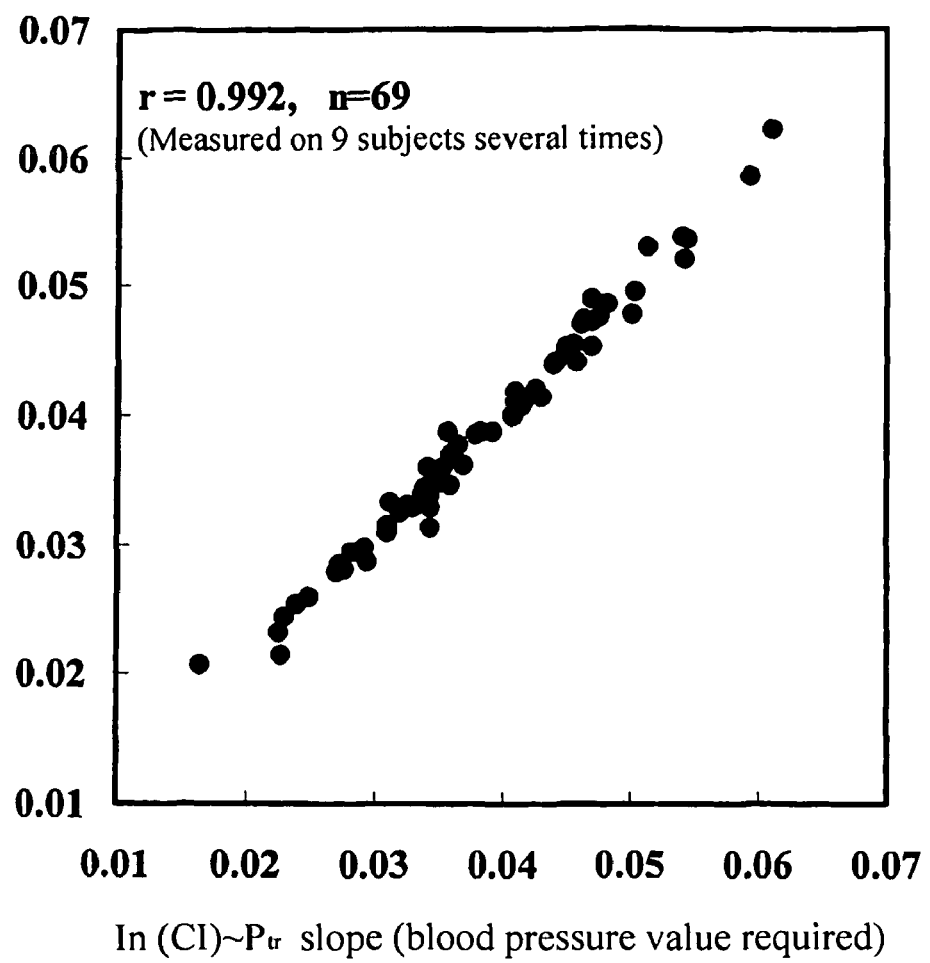

[Fig.4]
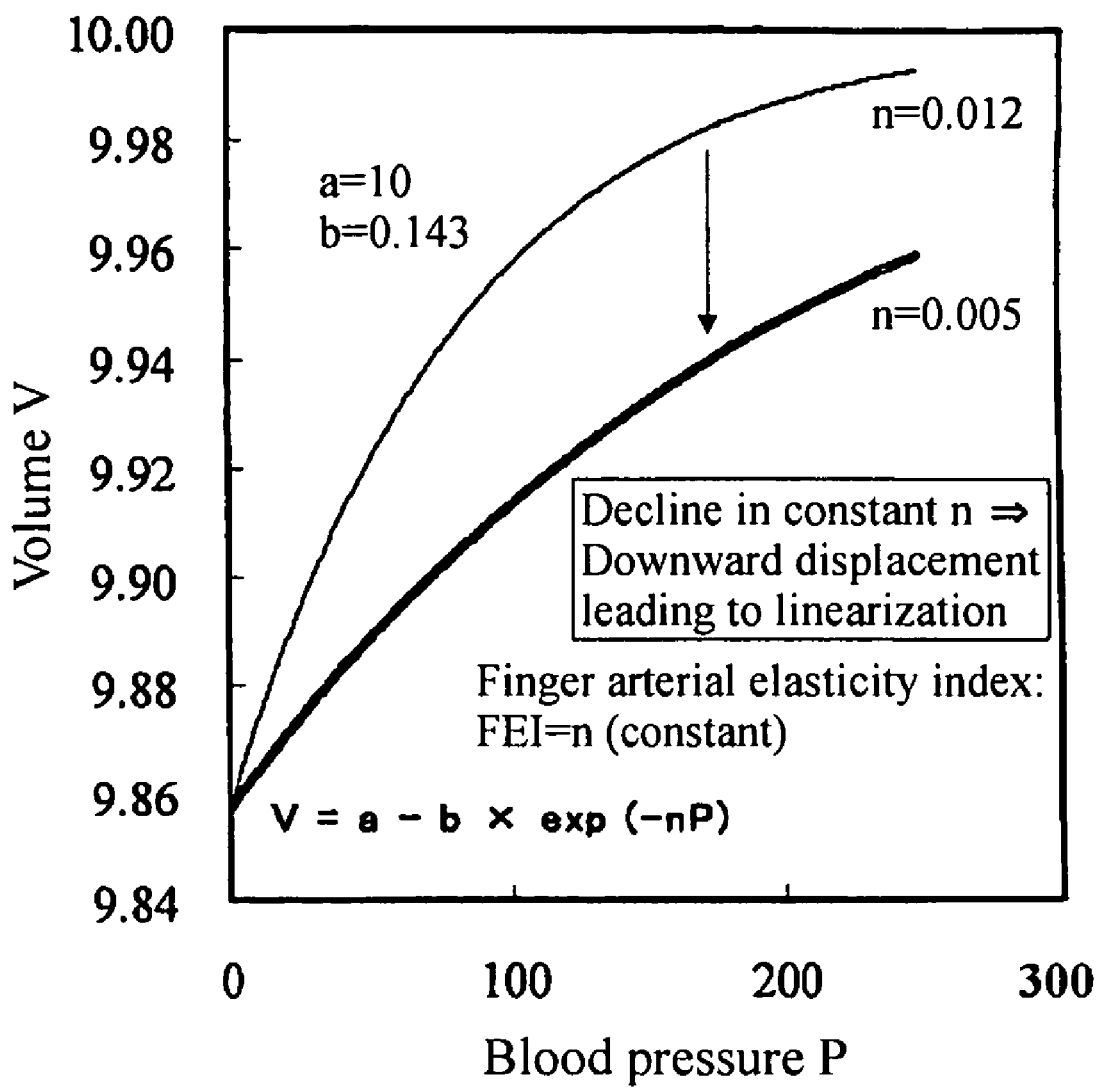

FINGER ARTERIAL ELASTICITY MEASURING PROGRAM, FINGER ARTERIAL ELASTICITY MEASURING DEVICE AND FINGER ARTERIAL ELASTICITY MESAURING METHOD

TECHNICAL FIELD

The present invention relates to a technology for evaluating the degree of arterial sclerosis, more particularly to a finger arterial elasticity measuring program, a finger arterial elasticity measuring device and a finger arterial elasticity measuring method suitable for readily measuring an elasticity index of a finger artery in accordance with a pulse wave of the finger artery.

BACKGROUND ART

A cardiovascular disease, at a precritical or even the earliest-phase level, is found with its particular symptoms characterized by a patient's functional and organic changes. Nowadays, the field of health science increasingly requires establishment of health condition's evaluation in the cardiovascular system and sufficient understanding of the correlations between particularly influential biological, psychological and social factors, using a marker for recognizing a sign thereof. Accordingly, simple noninvasive health evaluation method should be preferably introduced to carry out large-scale investigations of cardiovascular diseases. In response thereto, the inventors have focused on two markers used in the treatment of cardiovascular diseases: vascular endothelial function and vascular elasticity, and finally proposed a finger arterial elasticity evaluation method as a new simple health evaluation index, based on plethysmogram application technique.

A conventional technology for evaluating the degree of arterial sclerosis is disclosed in e.g., Japanese Unexamined Patent Application Publication No. 2004-236730 (Patent Document 1) as an invention of an arteriosclerosis evaluation apparatus for calculating an arteriosclerosis index as the degree of arterial sclerosis. The arteriosclerosis evaluation apparatus comprises pulse wave velocity information determining means for determining pulse wave velocity information related to the velocity of a pulse wave propagating in an artery of a living organism in accordance with a pulse wave signal detected from the living organism, blood pressure value determining means for determining a blood pressure value of the living organism in accordance with a cuff pulse wave signal from a cuff wound around said living organism and arteriosclerosis index calculating means for calculating an arteriosclerosis index as the degree of arterial sclerosis of said living organism from said pulse wave velocity information and said blood pressure value.

[Patent Document 1]

Japanese Unexamined Patent Application Publication No. 2004-236730

DISCLOSURE OF THE INVENTION

Problem to be Solved

However, conventional techniques, including the invention described herein, are prone to low reliability in evaluating the degree of arterial sclerosis based on the pulse wave velocity, because the propagation velocity is significantly affected by arterial diameter and blood concentration.

Under the circumstances, the inventors proposed finger arterial elasticity index (FEI) as a new index for evaluating the degree of arterial sclerosis without using less reliable pulse wave velocity. This FEI was invented according to an experiment (Joji Andoh, Kenichi Yamagoshi and Ryo Kamiya, Kodenshiki myakuhakeisoku no ohyoh, (Application of photoelectric pulse wave measurement), BME4 (4): 24-32 (1990)). Specifically, this experiment found that a function showing the relationship between a volume and a blood pressure of a finger artery, which is observed as a curve in a healthy person, demonstrates a linear (and flat) characteristic and also a gentle slope due to arterial sclerosis, aging or coronary artery disease.

FEI calculation requires, as described below in detail, measurement of a wide range of pressure value on a finger artery, and accordingly data of a pulse wave acquired by plethysmogram and a blood pressure continuously acquired by continuous sphygmomanometer.

However, since the above-mentioned continuous sphygmomanometer can be employed for test and research purposes, it is difficult to introduce in hospitals and many other medical institutions as a large and expensive apparatus. In reality, such introduction, if any, involves a limited number of apparatuses as well as longer measurement duration for a patient, thereby causing a difficulty in concurrently measuring data for many patients as opposed to physical examination and thus least practical use.

In order to solve the aforementioned problems, this invention provides a finger arterial elasticity measuring program, a finger arterial elasticity measuring device and a finger arterial elasticity measuring method for making it possible to measure an elasticity index of a finger artery in accordance with a pulse wave of a finger artery without measuring a blood pressure in evaluating the elasticity of the finger artery related to the degree of arterial sclerosis in an easy and least expensive manner.

Means for Solving the Problem

A finger arterial elasticity measuring program according to the present invention is characterized by a finger arterial elasticity measuring program for measuring the elasticity of a finger artery in accordance with a pulse wave of a finger artery and a computer functioning by the program, wherein the computer comprises: a pulse wave data memory unit which stores pulse wave data of a finger artery; a cuff pressure data memory unit which stores a cuff pressure of a cuff pressing the finger artery; a normalized pulse volume (NPV) calculating unit which acquires an amplitude ($\Delta I$) of an alternate component of a pulse wave and an average value of direct components (I) of the pulse wave from said pulse wave data memory unit and divides said amplitude ($\Delta I$) by the average value of said direct components (I) to calculate NPV; a relative cuff pressure ($P_r$) calculating unit which acquires a cuff pressure from said cuff pressure data memory unit to calculate a difference between a cuff pressure at the maximum amplitude of the pulse wave and each cuff pressure as $P_r$; and an FEI calculating unit which calculates a linear regression slope (n) of the following expression (1) as an elasticity index of the finger artery: $\ln(NPV)=\ln(bn)-n \cdot P_r$ (1) where b is a constant.

A finger arterial elasticity measuring device according to the present invention is characterized by a finger arterial elasticity measuring device for measuring the elasticity of a finger artery in accordance with a pulse wave of a finger artery, comprising a pulse wave data memory unit which stores pulse wave data of a finger artery, a cuff pressure data memory unit which stores a cuff pressure of a cuff pressing the finger artery, a normalized pulse volume (NPV) calculating unit which acquires an amplitude (ΔI) of an alternate component of a pulse wave and an average value of direct components (I) of the pulse wave from said pulse wave data memory unit and divides said amplitude (ΔI) by the average value of said direct components (I) to calculate NPV, a relative cuff pressure ($P_r$) calculating unit which acquires a cuff pressure from said cuff pressure data memory unit to calculate a difference between a cuff pressure at the maximum amplitude of the pulse wave and each cuff pressure as $P_r$, and an FEI calculating unit which calculates a linear regression slope (n) of the following expression (1) as an elasticity index of the finger artery (FEI): $ln(NPV)=ln(bn)-n \cdot P_r$ (1) where b is a constant.

A finger arterial elasticity measuring method according to the present invention is characterized by a finger arterial elasticity measuring method for measuring the elasticity of a finger artery in accordance with a pulse wave of a finger artery, comprising a pulse wave data memory step for acquiring pulse wave data of a finger artery from pulse wave detecting means and storing the data in the pulse wave data memory unit, a cuff pressure data memory step for acquiring a cuff pressure from finger pressing means and storing the data in the cuff pressure data memory unit, a normalized pulse volume (NPV) calculating step for acquiring an amplitude (ΔI) of an alternate component of a pulse wave and an average value of direct components (I) of the pulse wave from said pulse wave data memory unit and dividing said amplitude (ΔI) by the average value of said direct components (I) to calculate NPV, a relative cuff pressure ($P_r$) calculating step for acquiring a cuff pressure from said cuff pressure data memory unit to calculate a difference between a cuff pressure at the maximum amplitude of the pulse wave and each cuff pressure as $P_r$, and an FEI calculating step for calculating a linear regression slope (n) of the following expression (1) as an elasticity index of the finger artery (FEI):

$$ln(NPV)=ln(bn)-n \cdot P_r \quad (1)$$

where b is a constant.

Advantageous Effect of the Invention

The present invention can measure an elasticity index of a finger artery in accordance with pulse wave data of a finger artery without measuring a blood pressure in evaluating the elasticity of the finger artery closely related to the degree of arterial sclerosis in an easy and least expensive manner.

BEST MODE FOR CARRYING OUT THE INVENTION

A finger arterial elasticity measuring program, a finger arterial elasticity measuring device and a finger arterial elasticity measuring method according to the present invention are a program, an apparatus and a method, respectively suitable for calculating finger arterial elasticity index (FEI) as a new index to evaluate the degree of arterial sclerosis proposed by the inventors. The descriptions start with a method for calculating the above FEI.

As described above, the inventors derived the FEI, by introducing a function showing the relationship between a volume and a blood pressure of a finger artery which is normally formed of a curve but demonstrates a linear (and flat) characteristic and then a gentle slope due to arterial sclerosis, aging or coronary artery disease according to experimental results.

Specifically, the relationship between blood pressure (P) and volume (V) of a finger artery is approximated by the following expression (2) to represent the elastic force characteristic of a finger artery by three constants a, b and n.

$$V=a-b \times exp(-nP) \quad (2)$$

As shown in FIG. 4, it is confirmed that reduction in elastic force of a finger artery due to arterial sclerosis or aging corresponds to decline in the above constant n. The constant n is defined as finger arterial elasticity index (FEI).

Differentiating the above expression (2) by blood pressure (P) and converting it into logarithm, the following expression (3) is derived.

$$ln(\Delta V/\Delta P)=ln(bn)-nP \quad (3)$$

According to this expression, a natural logarithm of compliance (ΔV/ΔP), as a ratio of volume change to pressure change, shows a linear relationship with a blood pressure. Said compliance (ΔV/ΔP) is an index indicating the abilities of a finger artery to transform, be soft and elastic, etc.

Meanwhile, using the Lambert-Beer's law for photoelectric plethysmogram in a finger artery, the following expression (4) is given on variation in the pulse of all blood vessel volumes (ΔV).

$$\Delta V=(\epsilon C)^{-1} \cdot (\Delta I/I) \quad (4)$$

where ε is an average absorption coefficient for all bloods running in both arteries and veins, C is an average concentration for all bloods, ΔI is a pulsatile change in transmitted light volume indicated by an alternate component of a pulse wave (pulse volume), and I is a transmitted light volume of a finger (composed of tissues and blood running therein) indicated by direct components of the pulse wave.

Here, since the absorption coefficients of oxyhemoglobin and deoxyhemoglobin are identical at a wavelength of 810 nm (Van Assen delft, 1970), ε is constant within and between subjects irrespective of the arterio-venous balance of the blood content. It is also reported that the C value slightly changes by several percents after making a comparison between the cases in which a patient is relaxed and mentally stressed (Allen and Patterson, 1995; Muldoon et al., 1992). According to the above expression (4), (ΔI/I), which is approximately proportional to ΔV, is defined as a normalized pulse volume (NPV).

The compliance (ΔV/ΔP) can be expressed by the following expression (5) according to the NPV and the above expression (4).

$$(\Delta V/\Delta P)=(\epsilon C)^{-1} \cdot NPV/\Delta P \quad (5)$$

When (NPV/ΔP) is defined as a compliance index (CI), CI is proportional to the compliance. Therefore, the compliance (ΔV/ΔP) in the above expression (3) can be replaced with CI.

Additionally, blood pressure P on right side in the above expression (3) will be described. Transmural pressure $P_{tr}$ is calculated by dividing a mean blood pressure by a cuff pressure as an effective pressure of a finger artery when a finger is pressed. The transmural pressure $P_{tr}$ can be determined at a wide range of values by controlling the cuff pressure. Using these parameters to be measured, the above expression (3) can be replaced with the following expression (6).

$$ln(CI)=ln(bn)-n \cdot P_{tr} \quad (6)$$

A pair of data ($P_{tr}$ and CI) in the expression (6) can be measured by finger occluding maneuver. Specifically, as a pulse wave is measured by plethysmogram with a finger pressed by a cuff, etc. at a predetermined pressure value, a blood pressure is continuously measured by continuous sphygmomanometer, resulting in collection of a pair of data ($P_{tr}$ and CI). Then, regression analysis therefor using the above expression (6) will calculate a regression line gradient (n) as a finger arterial elasticity index (FEI). The FEI is found to have a significant correlation with a pulse wave velocity as an arterial sclerosis index in 31 healthy young male subjects (r=−0.407, p<0.05) (Masami Horiguchi, Goichi Tanaka, Kenta Matsumura, Takako Okayasu: Shinkekkankei no atarashii kanikenkohyokaho toshiteno shibidomyakudanseitokuseibunseki (Finger arterial elasticity, a novel assessment of cardiovascular health)—Seinenniokeru seisa oyobi myakuhasokudo tono sokankankei (Gender differences and correlation with brachial-ankle pulse wave velocity)—The Japanese Journal of Health Psychology, Vol. 19 (1): pp. 37-47, 2006). The unknown constants in the above expression (4), $\epsilon$ and C, change y intercept of a regression formula in the above expression (6), but have no impact on regression line gradient (FEI). Consequently, it is found that FEI is not affected by blood concentration of a subject.

As described above, however, precise and continuous measurement of blood pressure cannot lead to practical use due to requirement of large and expensive continuous sphygmomanometer. In fact, it is significantly difficult to introduce this apparatus in this invention as a method for widely investigating and evaluating the state of health of the cardiovascular system. To solve this technical problem, the inventors found out a method for accurately calculating FEI merely in accordance with pulse wave data under specific conditions through more detailed study.

Specifically, they found that since a mean blood pressure of a finger pressed slightly varies, assuming that the mean blood pressure is constant, transmural pressure $P_{tr}$ in the above expression (6) (mean blood pressure minus cuff pressure) corresponds to a relative cuff pressure $P_r$. Here, a relative cuff pressure $P_r$ at a particular time is defined as a difference between a cuff pressure at the maximum amplitude of the pulse wave and a cuff pressure at the particular time.

Since pulse pressure has no impact on slope, assuming that a pulse pressure of a finger pressed is constant, a linear regression slope of a normalized pulse volume (NPV) recorded per heartbeat to a relative cuff pressure $P_r$ in the same finger-pressing measurement trial is identical to a linear regression slope of compliance index (CI) to transmural pressure $P_{tr}$. It was found that if the above two assumptions are proved true, regression line gradient (n) in the following expression (1) corresponds to the FEI.

$$ln(NPV)=ln(bn)-n \cdot P_r \quad (1)$$

where b is a constant

According to the above FEI calculating method, a finger arterial elasticity measuring program, a finger arterial elasticity measuring device and a finger arterial elasticity measuring method according to the present invention are designed to readily perform FEI calculation processing.

An embodiment of a finger arterial elasticity measuring program, a finger arterial elasticity measuring device and a finger arterial elasticity measuring method according to the present invention will be described with reference to the drawings.

FIG. 1 is a block diagram indicative of overall configuration of a finger arterial elasticity measuring device 1 of this embodiment. As shown therein, the finger arterial elasticity measuring device 1 of this embodiment essentially comprises finger pressing means 2 for pressing a finger, pulse wave detecting means 3 for detecting a pulse wave, memory means 4 for storing the finger arterial elasticity measuring program of this embodiment and relevant data and operation processing means 5 for controlling each of these constitutive means and acquiring relevant data to perform operation processing.

Each of the constitutive means will be described in more detail. The finger pressing means 2 presses a human finger at a predetermined pressure value. The finger pressing means 2 in this embodiment comprises a tubular finger cuff 21 which is attached to a finger and an air pump 22 which feeds air to the finger cuff 21. The finger pressing means 2 can control the operation of the air pump 22 through the operation processing means 5 and determine a cuff pressure in an adjustable manner.

The pulse wave detecting means 3 detects a plethysmogram showing change in the volume of a finger artery. In this embodiment, the pulse wave detecting means 3 comprises a photoelectric sensor 31 which detects a light volume and a pulse wave amplifier 32 which amplifies an output signal transmitted from the photoelectric sensor 31. Herein, the photoelectric sensor 31 comprises a light emitting unit 31a which is disposed on the dorsal side of a finger and a light receiving unit 31b which is disposed on the ventral side of a finger at a position opposite to the light emitting unit 31a. The pulse wave amplifier 32 transmits amplified pulse wave data to a pulse wave data memory unit 42 described later.

The memory means 4 essentially comprises hard disk and random access memory (RAM), furthermore comprising a program memory unit 41 which stores a finger arterial elasticity measuring program of this embodiment, a pulse wave data memory unit 42 and a cuff pressure data memory unit 43. The pulse wave data memory unit 42 stores pulse wave data acquired from the pulse wave amplifier 32. The cuff pressure data memory unit 43 stores data of a cuff pressure adjusted by a cuff pressure control unit 51 described later.

The operation processing means 5 essentially comprises central processing unit (CPU). The operation processing means 5 executes the finger arterial elasticity measuring program stored in the program memory unit 41 to function as a cuff pressure control unit 51 which controls a cuff pressure by the finger pressing means 2, an NPV calculating unit 52 which calculates a normalized pulse volume (NPV), a relative cuff pressure calculating unit 53 which calculates a relative cuff pressure and an FEI calculating unit 54 which calculates a finger arterial elasticity index (FEI).

Each component of the operation processing means 5 will be described in more detail. The cuff pressure control unit 51 controls the driving of the air pump 22 to determine a cuff pressure by the finger cuff 21 in an adjustable manner. In this embodiment, the cuff pressure control unit 51 increases the cuff pressure from 0 with a constant speed for 20 seconds before and after the amplitude of a pulse wave reaches maximum and then finger is unpressed for 10 seconds (cuff pressure=0). This operation of the cuff pressure control unit 51 is defined as one trial and repeated predetermined times to control the finger pressing means 2. Herein, the cuff pressure control unit 51 constantly acquires cuff pressure data and stores the data in the cuff pressure data memory unit 43.

The NPV calculating unit 52 calculates the above-described normalized pulse volume NPV (=$\Delta I/I$). Here, a transmitted light volume ($\Delta I$) by the variation in the pulse is determined by an amplitude of an alternate component of a pulse wave. A transmitted light volume (I) of a finger (composed of tissues and blood running therein) is determined by an average value of direct components of the pulse wave at the same time. Consequently, the NPV calculating unit 52 acquires pulse wave data from the pulse wave data memory unit 42 and divides the amplitude of an alternate component of a pulse wave by the average value of direct components of the pulse wave at the same time to calculate an NPV.

The relative cuff pressure calculating unit 53 calculates the above described relative cuff pressure $P_r$. In this embodiment, a relative cuff pressure $P_r$ at a particular time is defined as a difference between a cuff pressure at the maximum amplitude of a pulse wave and a cuff pressure at the particular time. Therefore, the relative cuff pressure calculating unit 53 first acquires pulse wave data from the pulse wave data memory unit 42 and detects the time when the amplitude of a pulse wave reaches maximum, specifically the time when transmural pressure $P_{tr}$ becomes 0. Then, the relative cuff pressure calculating unit 53 acquires cuff pressure data from the cuff pressure data memory unit 43 and determines a difference between a cuff pressure at the maximum amplitude of a pulse wave and a cuff pressure at a particular time to calculate a relative cuff pressure.

The FEI calculating unit 54 calculates the above described finger arterial elasticity index (FEI). Herein, the FEI is expressed as regression line gradient (n) in the above expression (1). Accordingly, the FEI calculating unit 54 acquires a pair of data (NPV and relative cuff pressure) from the NPV calculating unit 52 and the relative cuff pressure calculating unit 53, respectively and performs regression analysis for the above expression (1) to calculate FEI.

In this embodiment, the memory means 4 stores a print table (e.g. soft, normal, hard) indicating the elasticity of a finger artery with reference to FEI digit number. In accordance with an FEI value calculated by the FEI calculating unit 54, elasticity data of the finger artery are outputted from indicating means (not shown) and printing means.

Next, the operation of the finger arterial elasticity measuring device 1 executed by the finger arterial elasticity measuring program of this embodiment and the finger arterial elasticity measuring method will be described with reference to FIG. 2.

When the finger arterial elasticity measuring device 1 of this embodiment measures the elasticity of a finger artery, a photoelectric sensor 31 is first attached to a forefinger of a subject between the 2nd and 3rd joints and a finger cuff 21 is attached to a finger so as to cover the photoelectric sensor 31 (step S1). A light emitting unit 31a of the photoelectric sensor 31 is attached on the dorsal side of the finger and a light receiving unit 31b is attached on the ventral side of the finger at a position opposite to the light emitting unit 31a. In this manner, the volume of transmitted light through the finger by the light emitting unit 31a is detected by the light receiving unit 31b.

Subsequently, when the cuff pressure control unit 51 starts the driving of the air pump 22, air fed from the air pump 22 inflates the finger cuff 21 to press the forefinger (step S2). In this embodiment, after the cuff pressure control unit 51 increases a cuff pressure from 0 with a constant speed during one trial for 20 seconds, the finger is unpressed and the operation is stopped for 10 seconds. This operational control is repeated several times. During each trial, several pulses required for regression analysis can be obtained.

As the finger pressing means 2 presses the finger, light is emitted from the light emitting unit 31a of the photoelectric sensor 31. Thus, the light receiving unit 31b detects the volume of light transmitted through finger tissues or blood vessels. Here, hemoglobin in the blood has an absorption spectrum specific for light within a wavelength range. In a living organism, the volume of transmitted light irradiated with light within the wavelength range changes according to hemoglobin volume which varies as the volume of a blood vessel changes. By amplifying the transmitted light volume by the pulse wave amplifier 32, a pulse wave can be detected (step S3).

Next, the NPV calculating unit 52 acquires pulse wave data from the pulse wave data memory unit 42 and divides an amplitude of an alternate component by an average value of direct components to calculate an NPV (step S4). In accordance with pulse wave data acquired by the relative cuff pressure calculating unit 53 from the pulse wave data memory unit 42, the time when the amplitude of a pulse wave reaches maximum is detected and a difference between a cuff pressure at the time and a cuff pressure at a particular time is determined to calculate a relative cuff pressure $P_r$ (step S5).

The FEI calculating unit 54 acquires plural pairs of data (NPV and relative cuff pressure) from the NPV calculating unit 52 and the relative cuff pressure calculating unit 53, respectively and performs regression analysis for the above expression (1) to calculate an FEI (step S6). Then, the FEI calculating unit 54 calculates FEI merely based on pulse wave, without using blood pressure value.

Subsequently, an example of the finger arterial elasticity measuring program, the finger arterial elasticity measuring device 1 and the finger arterial elasticity measuring method according to the present invention will be described.

EXAMPLE

In this example, a test was conducted to confirm the degree to which FEI obtained in this invention corresponds to FEI obtained as a linear regression slope in the above expression (6).

This example employs a light-emitting diode (L810-40K00, Ebisu Electronics) with a wavelength of 810 nm as the light emitting unit 31a of the photoelectric sensor 31 and a photodiode (HPI-2464R5, Kodenshi Corp.) as the light receiving unit 31b. A commercially available pulse wave amplifying apparatus (MPN1001, Medisens, INC.) was employed as the pulse wave amplifier 32.

In addition, a noninvasive continuous blood pressure measuring apparatus (JENTOW-7700, Japan Korin) was employed as a continuous sphygmomanometer for measuring a blood pressure required for calculating a linear regression slope in the above expression (6). A continuous blood pressure waveform obtained from the continuous sphygmomanometer and a pulse wave obtained from the pulse wave amplifier 32 were recorded in a personal computer (PC) via a bioelectric amplifying unit (1253A, NEC Sanei) and AD-converted at 16 bit with a sampling time of 1 ms. For PC analysis, waveform signal processing language (LabVIEW 7.1, National Instrument) was used.

This example employs the finger arterial elasticity measuring device 1 as configured above to collect required data from 9 subjects several times. Specifically, after a cuff pressure of the finger cuff 21 attached to each subject's finger was gradually increased with a speed of approx. 6 mmHg/s for 20 seconds, one trial of releasing a cuff pressure for 10 seconds was repeated 8 times every 30 seconds. Then, as the finger was pressed, plural pairs of data ($P_r$ and CI) were collected.

Using these pairs of data, regression analysis was performed for the above expressions (6) and (1) during each trial to define an average value of calculated linear regression slopes as FEI. FIG. 3 shows the results. As shown therein, it was found that FEI in this invention calculated merely by pulse wave data (a linear regression slope of the above expression (1)) corresponds to FEI calculated using blood pressure data (linear regression slope of the above expression (6)) with a significantly high precision.

The above embodiment can provide the following advantages:
1. FEI index on the elasticity of a finger artery merely in accordance with a pulse wave of a finger artery can be measured in an easy and least expensive manner.
2. With no need for measuring a blood pressure, preparation of large and expensive continuous sphygmomanometer is not necessary to measure FEI.
3. In comparison with blood pressure measurement, this invention can concurrently obtain necessary data from many patients in e.g. medical examination due to shorter measuring time for a patient.

A finger arterial elasticity measuring program, a finger arterial elasticity measuring device 1 and a finger arterial elasticity measuring method according to the present invention are not limited in the above described embodiment, but may be altered accordingly.

BRIEF DESCRIPTION OF THE DRAWINGS

The above and other objects in this invention will be seen by reference to the description taken in connection with the drawings, in which:

FIG. 1 is a block diagram indicative of one embodiment of a finger arterial elasticity measuring device according to the present invention;

FIG. 2 is a flow chart indicative of a finger arterial elasticity measuring method of this embodiment;

FIG. 3 is a graph indicative of a relationship between FEI (longitudinal axis) in this embodiment and FEI (lateral axis) calculated using blood pressure data; and FIG. 4 is a graph indicative of a relationship between blood pressure (lateral axis) and volume (longitudinal axis) on a finger artery.

EXPLANATION OF LETTERS OR NUMERALS

1 Finger arterial elasticity measuring device
2 Finger pressing means
3 Pulse wave detecting means
4 Memory means
5 Operation processing means
21 Finger cuff
22 Air pump
31 Photoelectric sensor
31a Light emitting unit
31b Light receiving unit
32 Pulse wave amplifier
41 Program memory unit
42 Pulse wave data memory unit
43 Cuff pressure data memory unit
51 Cuff pressure control unit
52 NPV calculating unit
53 Relative cuff pressure calculating unit
54 FEI calculating unit

The invention claimed is:

1. A non-transitory, computer-readable medium having program instructions embodied thereon for measuring an elasticity of a finger artery in accordance with a pulse wave of a finger artery, wherein the instructions, when executed by a processor, causes the processor to perform a plurality of steps comprising:

storing pulse wave data of a finger artery in a pulse wave data memory unit;
storing a cuff pressure of a cuff pressing the finger artery in a cuff pressure data memory unit;
calculating a normalized pulse volume (NPV) in an NPV calculating module that acquires an amplitude ($\Delta I$) of an alternating component of a pulse wave and an average value of direct components (I) of the pulse wave from said pulse wave data memory unit and divides said amplitude ($\Delta I$) by the average value of said direct components (I) to calculate NPV;
calculating a relative cuff pressure ($P_r$) in a $P_r$ calculating module that acquires a cuff pressure from said cuff pressure data memory unit and calculates a difference between a cuff pressure at a maximum amplitude of a pulse wave and each cuff pressure as $P_r$; and
calculating a linear regression slope (n) in a finger elasticity index calculating module using the following expression as an elasticity index of the finger artery (FEI):
$\ln(NPV) = \ln(b \cdot n) - n \cdot P_r$, where b is a constant.

2. A finger arterial elasticity measuring device which measures an elasticity of a finger artery in accordance with a pulse wave of a finger artery, comprising:

a pulse wave data memory unit which stores pulse wave data of a finger artery;
a cuff pressure data memory unit which stores a cuff pressure of a cuff pressing the finger artery;
a normalized pulse volume (NPV) calculating unit which acquires an amplitude ($\Delta I$) of an alternating component of a pulse wave and an average value of direct components (I) of the pulse wave from said pulse wave data memory unit and divides said amplitude ($\Delta I$) by the average value of said direct components (I) to calculate NPV;
a relative cuff pressure ($P_r$) calculating unit which acquires a cuff pressure from said cuff pressure data memory unit to calculate a difference between a cuff pressure at a maximum amplitude of a pulse wave and each cuff pressure as $P_r$; and
a finger elasticity index calculating unit which calculates a linear regression slope (n) of the following expression as an elasticity index of the finger artery (FEI):
$\ln(NPV) = \ln(b \cdot n) - n \cdot P_r$, where b is a constant.

3. A method for measuring finger arterial elasticity which measures an elasticity of a finger artery in accordance with a pulse wave of a finger artery, comprising:

acquiring pulse wave data of a finger artery from a pulse wave detecting means;
storing the pulse wave data in a pulse wave data memory unit;
acquiring cuff pressure data from a finger pressing means, storing the cuff pressure data in a cuff pressure data memory unit;
calculating a normalized pulse volume (NPV) in a processor by acquiring an amplitude ($\Delta I$) of an alternating component of a pulse wave and an average value of direct components (I) of the pulse wave from said pulse wave data memory unit and dividing said amplitude ($\Delta I$) by the average value of said direct components (I) to calculate NPV;
(Pr) calculating a relative cuff pressure ($P_r$) in said processor by acquiring a cuff pressure from said cuff pressure data memory unit by calculating a difference between a cuff pressure at a maximum amplitude of a pulse wave and each cuff pressure as $P_r$; and
calculating a linear regression slope (n) in said processor using the following expression as an elasticity index of the finger artery (FEI):
$\ln(NPV) = \ln(b \cdot n) - n \cdot P_r$, where b is a constant.

* * * * *